United States Patent [19]

Posner et al.

[11] Patent Number: 4,994,375
[45] Date of Patent: Feb. 19, 1991

[54] STABLE HUMAN SERUM BASED CONTROL AND/OR CALIBRANT

[75] Inventors: Alan Posner, Davie; Pedro Romero, Miami, both of Fla.

[73] Assignee: Baxter International Inc., Deerfield, Ill.

[21] Appl. No.: 217,243

[22] Filed: Jul. 11, 1988

[51] Int. Cl.$^5$ ............................ C12Q 1/32; C12Q 1/50
[52] U.S. Cl. ........................................ 435/17; 435/26; 435/188; 436/8; 436/15; 436/18
[58] Field of Search .................... 435/188, 26, 11, 15; 436/8, 15, 18

[56] References Cited

U.S. PATENT DOCUMENTS 4,118,279  6/1978  Determan et al.
4,339,533  7/1982  Chu.
4,684,615  8/1987  Hoskins ................................ 436/16

OTHER PUBLICATIONS

Al-Mudhaffer and Rassam, *Biochemistry and Experimental Biology*, 15:237–244, 1979.
Tietz, ed., *Textbook of Clinical Chemistry*, W. B. Saunders Co., Philadelphia, pp. 678 and 686, 1976.
Udall, *Scand. J. Clin. Lab. Invest.*, 44:223–229, 1984.
Wu, *Clin. Chem.*, 30:1718–1719, 1984.
Boone et al., "An Interlaboratory Study of . . . ", Clinical Chemistry, vol. 26, (1980), pp. 513–519.
Fisher Scientific 1983 Catalog, pp. 313, 319, 613, 612 and 625.
White et al., *Principles of Biochemistry*, McGraw-Hill, Inc., N.Y., 1973, p. 101.
DiGiorgio, Jr., "Determination of Serum Lactic Dehydrogenase . . . ", Clinical Chemistry, vol. 17, (1971), pp. 326–331.
C. Chervenka, "The Urea Denaturation of Chymotrypsinogen as Determined by Ultraviolet Spectral Changes, the Influence of pH and Salt", 82 J. Am. Chem. Soc. 582 (1960).
G. DiSabato, "The Denaturation of Lactic Dehydrogenases", J. Bio. Chem., 1072 (1965).
J. Gordon et al., "The Relationship of the Effectiveness of Denaturing Agents for Proteins", 2 Denaturants Prot. 47 (1962).
Harrington et al., "The Effects of Concentrated Solutions of Lithium Bromide on the Configuration of Polypeptides and Proteins", 30 Compt. Rend. Trav. Labs., Carlsberg Ser. Chim 167 (1957).
O. Hetland, "Activation of Creatine Kinase Activity in Lyaphilized Control Materials", 37 Scand. J. Clin. Lab. Invest. 563 (1977).
Hissin et al., "Stability of Total Lactate Dehydrogenase (LD) and LD Isoenzymes at Different Storage Temperatures as a Function of Time", 3L Clin. Chem. 999 (1985).
Kar et al., "Activation of Cratine Phosphokinase by Normal and Muscular Dystrophy Sera".
Kreutzer et al., "Lactic Dehydrogenase Isoenzyme in Blood Serum After Storage at Different Temperatures", 9 Clin. Chim. Acta 64 (1964).
Miyada, "Creatine Kinase Reactivation by Thiol Compounds", 58 Clinica Chimico Acta 97 (1975).
Morin, "Creatine Kinase: Stability, Inactivation, Reactivation", 23 Clin. Chem. 646 (1977).
Nagy et al., "Depolymerization of F-Actin by Salts & Amides", 23 Federation Proc. 530 (1964).
Nealon et al., "Stability of Commonly Used Thiols and of Human Creatine Kinase Isoenzymes during Storage at Various Temperatures in Various Media", 23 Clin. Chem. 816 (1977).
Shain et al., "Creatine Kinase & Lactate Dehydrogenase: Stability of Isoenzymes and their Activity in Stored Human Plasma and Prostatic Tissue Extracts and Effects of Sample Dilutions", 29 Clin. Chem. 832 (1983).
R. Simpson et. al., "The Kinetics of Protein Denaturation, I. The Behavior of the Optical Rotation of Ovalbumin in Urea Solutions", 75 J. Am. Chem. Soc. 5139 (1953).
Von Hippel et al., "Neutral Salts: The Generality of their Effects on the Stability of Macromolecular Conformation", 145 Science 577 (1964).
W. Warren, "Activation of Serum Creatine Kinase by Dithiothreitol", 18 Clin. Chem. 472 (1972).

*Primary Examiner*—Esther L. Kepplinger
*Assistant Examiner*—Jacintha M. Stall
*Attorney, Agent, or Firm*—Susan Bennett Fentress; Paul C. Flattery; Marjorie D. Hunter

[57] ABSTRACT

A stable human serum based control for the assay of Total LD and CK and their isoenzymes. This control may be lyophilized and reconstituted and still provide the same enzyme activity prior to lyophilization, for seven (7) days after reconstitution, if stored in the dark at or about 2°0 to 8° C. No thiol compounds other than the amount normally used to purify CK isoenzymes are found in this highly stable control.

5 Claims, No Drawings

STABLE HUMAN SERUM BASED CONTROL AND/OR CALIBRANT

This invention generally relates to a reconstituted stable human serum based control to assist in the monitoring of the precision and accuracy of the following assays: total protein, CK (creatine kinase), CK isoenzymes, LD (lactate dehydrogenase), LD isoenzymes, and specific proteins.

BACKGROUND OF THE INVENTION

1. Field of the Invention

The claimed subject matter pertains to reconstituted stable human serum based controls and/or calibrants used to assist in the measurement of total protein, total CK, CK isoenzymes, total LD, LD isoenzymes, and specific proteins. In particular, the claimed subject matter pertains to a lyophilized stable human serum based control with long term shelf life and relatively long term reconstituted stability.

2. Description of the Related Art

A number of physiological conditions and states are correlated with the above enzymes. An elevated total CK level correlates with myocardial infarction, myocardial ischemia, stenocardia, tachycardia, myocarditis, subarachnoid hemorrage, stroke, brain tumor, convulsions, meningitis, encephalitis, acute psychosis, epilepcy, muscular dystropy, viral myositis, severe myoglobinurea, malignant hyperthermia, carbon monoxide poisioning, etc.

An increased level of the principle isoenzyme CK-MB is associated with myocardial infarction, myocardial ischemia, muscular dystrophy, myositis, severe myoglobinurea, malignant hyperthermia and carbon monoxide poisoning. Increased levels of CK-MM has no current clinical significance. The presence of LD, together with CK-MB, is quite specific for myocardial infarction. The isoenzymes of LD are also correlated with certain disease states.

Tests have been devised to determine the presence or concentration of these enzymes in bodily fluids. See e.g. NHL CK MB, NHL CK, NHL LD (DR 5020), ACA TM LDH pack, Paragon TM (Beckman) CK isoenzyme electrophoresis, etc.

In order to maintain the precision and accuracy of these tests, good laboratory practice dictates that control materials be included with patient samples each time an assay is run. If control values appear out of range, if upward or downward trends are noted, or if sudden shifts are seen in control values, all operating parameters, including instrument calibration, should be checked.

It has been observed, however, that CK and LD enzymes are not highly stable. In order to facilitate transport and storage of these tests the controls are lyophilized. It has also been observed that enzyme activity can also be lost during lypholization and reconstitution.

The enzyme CK, by virtue of its reactive SH group, is known to be one of the least stable enzymes. In order to preserve the enzyme activity of CK and other SH—containing enzymes one or more thiol-compounds are added to the CK solution. N. Kar, "Activation of Creatine Phosphokinase by Sulfydryl Compounds in Normal and Muscular Dystrophy Sera," 18 Proc. Exp. Bio. Med. 662, 663 (1985). D. Miyada, "Creatine Kinase Reactivation by Thiol Compounds", 58 Clinica Chimica Acta 97 (1975); G. Szasz, "Creatine Kinase in Serum: 5. Effect of Thiols on Isoenzyme Activity During Storage at Various Temperatures", 24 Clin. Chem. 1557 (1978). In addition to generally stabilizing CK, it is often desirable to lyophilized and reconstitute solutions containing this enzyme. A number of researchers suggest that reactivation should occur in the presence of added thio activator. O. Hetland, "Activation of Creatine Kinase Activity in Lyophilized Control Materials", 37 Scand. J. Clin. Lab. Invest. 563 (1977); L. Morin, "Creatine Kinase: Stability, Inactivation, Reactivation", 23 Clin. Chem. 646 (1977).

Another approach to stabilizing SH enzymes is through modification of the reactive —SH groups by some reagent. These reagents, e.g. iodoacetate, lead to irreversible reaction of the SH group and an undesirable loss of enzyme activity.

Still another approach to stabilizing SH enzymes involves reacting an organodisulfide, organothio sulfonate, tetrathionate or a mixture thereof with CK to form a stable intermediate composition for incorporating into a diagnostic reference standard. See U.S. Pat. No. 4,339,533.

In addition, it has been observed that salts and coenzymes can protect certain enzymes against denaturation. DiSabato studied the action of a number of organic and inorganic salts on the inactivation of chicken lactic dehydrogenase by urea. G. DiSabato, "The Denaturation of Lactic Dehydrogenases", 240 J. Biological Chem. 1072, 1073 (1965). It has also been observed that stability varies depending on the pH of the solution. C. Chervenka, "The Urea Denaturation of Chymotrypsinogen as Determined by Ultraviolet Spectral Changes; The Influence of pH and Salts", 82 J. Am. Chem. 582 (1960). In addition, it is known that the stability, as measured by a decrease in activity, of individual enzymes, varies as a function of time and storage temperature. P. Hissin et al., "Stability of Total Dehydrogenase (LD) and LD isoenzymes at Different Storage Temperatures as a Function of Time", 31 Clin. Chem. 999 (1985); H. Kreutzer "Lactic Dehydrogenase Isoenzymes in Blood Serum After Storage at Different Temperatures", 9 Clin. Chim. Acta 64 (1964).

BRIEF SUMMARY OF THE INVENTION

This invention relates to a stabilized clinical laboratory human serum based control and/or calibrants to be used in the monitoring of the precision and accuracy of the following assays: total protein, total CK (creatine kinase), CK isoenzymes, total LD, LD isenozymes, and specific proteins. In particular, the stabilized control shows the same enzymatic pattern after lypholization and reconstitution, as when examined freshly.

The control uses a novel mixture of constituents to impart increased stability. In particular, a mixture of fresh human serum and sodium citrate at a pH of 6.7 is used to stabilize the enzymes. Very surprisingly, no thiol compounds, in addition to the thiol compounds used during purification of the human CK enzymes, are added to the mixture.

DETAILED DESCRIPTION OF THE INVENTION AND BEST MODE OF OPERATION

Example I

1. Base Pool Preparation

Fresh human serum (quantity equals amount required to obtain 6.5 to 7.5 g/dl) mixed in a stainless steel container for fifteen (15) minutes. The pool is filtered through a suitable prefilter (E.G. Zeta Plus CPS-50, Ertel #3) into a clean stainless steel container. Antibiotics (Gentamicin 86 mg/l, cycloheximade 50 mg/l) and sodium citrate 8.8 g/l are added and the pool is mixed for fifteen (15) minutes. The pH of the pool is measured and adjusted to 6.7±0.1 with hydrochloric acid or 7N sodium hydroxide. The pool is filtered through an autoclaved filter set ending in a less than 0.3 micron filter into an appropriate sterile storage container and stored until needed at 2°-8° C. A base pool should not be stored for longer than six (6) days.

2. Preparation of Stabilized Enzymes

Human heart CK-MB (Lee Scientific) is added to the base pool and mixed for fifteen (15) minutes. The human CK enzymes obtained from Lee Scientific are purified by dialyzing human CK enzymes against 0.01M sodium phosphate, 0.01M EDTA, 0.001M thiol (dithiothreitol (DTT) or dithioerythreitol (DTE)). CK-MB concentration is adjusted to between 15-25% of the total CK concentration. The total CK concentration is from between 620-770 U/L (ACA) (approximately fifteen percent (15%) of activity is lost during lyophilization). Human heart CK-MM (Lee Scientific) is added to the base pool and mixed for fifteen (15) minutes. CK-MM concentration is adjusted to between 70 to 80% of total CK concentration. Human heart LD is added and the pool is mixed for fifteen (15) minutes. LDH concentration is adjusted to to 300 to 400 U/L. CK-BB comprises 2 to 10% of CK total, LD1, comprises 37 to 47% total LD, LD2 comprises 23 to 37% total LD, LD3 comprises 7 to 19% total LD, LD4 comprises 2 to 8% total LD and LD5 comprises 3 to 11% of total LD. These analytes are not adjusted because their values are usually present from the base material and spikes. The pool is brought to volumn with purified water and mixed for fifteen (15) minutes. The pool is filtered through a sterile less than 0.3 micron filter into a sterile container. The thiol concentration derived from added human CK enzymes should not exceed $3 \times 10^{-2}$M. Upon completion of steps 1 and 2 of Example I, the control is comprised of the following constituents:

TABLE I

| CK/LD CONTROL | | |
|---|---|---|
| Constituent | Method | Wet Target Range |
| Total Protein | aca | 6.5-7.5 g/dl |
| CK-MB[1] | aca & Paragon | 80-170 U/L[2] |
| CK, Total | aca | 620-770 U/L |
| LDH, Total | aca | 300-400 U/L |
| Sodium Citrate | | $1 \times 10^{-3}$ M |

[1]CK-MB = (ACA Total CK) (% MB from Paragon ™ (Beckman))
[2]Based upon Total CK ACA ™ Range of 620-770 U/L. Use 110 U/L as target.

3. Filling/Lyophilization

Within thirty-six (36) hours of the formulation and filling, the start of lyophilization must occur. Vials containing 1 mL of the formulated serum are frozen in a lyophilizer at a temperature of −37° C. The water in the frozen serum is sublimated under vacuum at a temperature of about +23° C. The bottles containing the lyophilized product are sealed under vacuum; and then stored at 4° C.

Unreconstituted material should be stored in the refrigerator at 2°-8° C. Reconstituted material is stable for five (5) days when stored tightly capped in the dark at 2°-8° C.

4. Reconstitute

To reconstitute the product: Remove the control from the refrigerator and allow it to come to room temperature (approximately ten (10) minutes). Carefully open the vial; using a Class A volumetric pipet, add exactly 1.00 mL of deionized (or distilled) water at room temperature. Stopper the vial and let it stand for ten (10) minutes at room temperature. Invert the vial gently at least three (3) times to ensure that the control is in solution and that the contents are thoroughly mixed. Store in the dark at 2°-8° C. Reconstituted product is tested for stability, i.e. activity of enzyme over time.

To determine reconstitution stability the following tests were conducted. From these tests one can see that upon reconstitution the enzymes show essentially the same characteristics as listed in Table I. The enzymes maintain these properties for at least seven (7) days.

TABLE II

| | Time | | |
|---|---|---|---|
| | 0 | 5 | 7 |
| Analyte | days post-reconstitution | | |
| Protein g/dl | 5.9 | 6.0 | 6.1 |
| Albumin g/dl | 3.6 | 3.7 | 3.8 |
| Protein Electrophoresis % | | | |
| Albumin | 57.4 | 59.5 | 58.5 |
| Alpha 1 glob | 2.6 | 2.3 | 2.5 |
| Alpha 2 glob | 8.8 | 9.4 | 9.6 |
| Beta | 12.7 | 12.0 | 11.9 |
| Gamma | 17.5 | 16.7 | 17.6 |
| LDH*, total U/L | 339 | 334 | 328 |
| LD-1 % | 56 | 59 | 60 |
| LD-2 | 28.5 | 28.5 | 28.1 |
| LD-3 | 9.6 | 8.5 | 8.9 |
| LD-4 | 3.0 | 2.0 | 2.2 |
| LD-5 | 2.7 | 2.2 | 1.7 |
| CK** | | | |
| CK-MM % | 66.8 | 66.0 | 66.8 |
| CK-MB | 29.5 | 29.7 | 29.5 |
| CK-BB | 3.5 | 4.2 | 3.7 |
| Specific Proteins mg/dL | | | |
| IgA | 180 | 179 | 181 |
| IgG | 1071 | 1058 | 1057 |
| IgM | 99 | 98 | 98 |
| C 3 Protein | 99 | 103 | 107 |
| C 4 Protein | 23.3 | 22.0 | 22.8 |
| Haptoglobin | 73.5 | 74.3 | 73.7 |
| Transferrin | 302 | 305 | 301 |
| Alpha-1-antitryp | 132 | 133 | 129 |
| Acidglycoprotein | 48.3 | 48.5 | 48.2 |
| Macroglobin | 143 | 144 | 145 |
| Ceruloplasmin | 28.2 | 27.8 | 27.3 |
| Apolipoprotein A-1 | 130 | 123 | 122 |
| Apolipoprotein B | 60.1 | 56.1 | 58.6 |
| Thyroid Function | | | |
| T 3 ng/dL | 81.6 | 84.6 | 81.6 |
| T 3 Uptake % | 35.5 | 33.8 | 34.5 |
| Thyroid Binding Globulin ug/mL | 19.8 | 20.8 | 20.3 |

*LDH stability is determined at a reference laboratory, NHL (DR 5020), on an Olympus Analyzer.
**CK activity is determined, for Arrhenius stability, on a DuPont ACA ™, "CK Pack".

EXAMPLE II

The stable reconstituted serum based control for Total LD and CK and their isomers prepared in Example I is used as a control in gel electrophoresis of a serum sample from a patient.

Beckman's Paragon ™ LD Isoenzyme Electrophoresis kit is intended for the diagnostic determination of the isoenzymes of LD in human serum. LD is composed of four polypeptide subunits. The various isoenzymes of LD can be distinguished on the basis of their subunit composition. Differences in subunit composition result in enzyme molecules with different charges. The differences in surface charge is the basis upon which the various isoenzymes can be separated by electrohporesis.

Electrophoresis of lactate dehydrogenase isoenzymes may be used as both a quantitative and a qualitative procedure. When analyzed quantitatively, the electrophoretic pattern is subjected to a densitometric scan, and the relative amounts of the different isoenzymes are calculated as percentages and finally expressed as International Units per liter (IU/L) of lactate dehydrogenase activity. When used as a qualitative procedure, each electrophoretic pattern is interpreted visually.

Accuracy of the results of can be assured by using the control described in Example I as follows:

The LDH pattern shows product stability over time. A electrophoretic separation was performed on product that had been reconstituted five (5) and seven (7) days prior to analysis. The separation is conducted in parallel with freshly reconstituted sample. The pattern was stable and reproducible which makes the product ideally suited for use as a control.

It should be understood that the specification and examples are illustrative but not limitative of the present invention and other embodiments with the spirit and scope of the invention will suggest themselves to those skilled in the art.

What is claimed is:

1. A stable reconstituted human serum based control for the assay total LD and CK and their isoenzymes, which comprises a mixture of:
   (a) fresh human serum in sufficient quantity to obtain a final total protein concentration from about 6.5 to 7.5 g/dl;
   (b) from about 525 to 695 U/L of total CK, said CK being comprised of about 70 to 80% CK-MM isoenzyme, about 15 to 25% CK-MB isoenzyme and about 2 to 10% CK-BB isoenzyme;
   (c) from about 300–400 U/L of LD, said LD being comprised of 37 to 47% LD1 isoenzyme, 23 to 37% LD2 isoenzyme, 7 to 19% LD3 isoenzyme, 2 to 8% LD4 isoenzyme, and 3 to 11% LD5 isoenzyme; and
   (d) an effective amount of sodium citrate to stabilize the said enzymes;
   (e) said control having no added thiol compounds other than the amount normally used to purify CK isoenzymes, said thiol compound concentration being less than $3 \times 10^{-2}$M and said purified CK being added to the control to meet the parameters specified in (1)(b).

2. The control of claim 1 wherein sodium citrate concentration is about $1 \times 10^{-3}$M.

3. The control of claim 1 having seven (7) day stability after being reconstituted, when stored in the dark at 2° to 8° C.

4. The control of claim 1 wherein the final pH is 6.7±0.1.

5. The process to monitor the precision and accuracy of an assay for an enzyme selected from the group consisting of total CK, total LD, CK-MM, CK-MB, CK-BB, LD1, LD2, LD3, LD4, and LD5, comprising conducting the assay for said enzyme in a sample, conducting the same assay using the control of claim 1 and comparing the values obtained.

* * * * *